US00PP28659P3

(12) United States Plant Patent
Meilland

(10) Patent No.: US PP28,659 P3
(45) Date of Patent: Nov. 21, 2017

(54) HYBRID TEA ROSE PLANT NAMED 'MEINOSTAIR'

(50) Latin Name: *Rosa hybrida*
Varietal Denomination: Meinostair

(71) Applicant: THE CONARD-PYLE COMPANY, West Grove, PA (US)

(72) Inventor: Alain A. Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 54 days.

(21) Appl. No.: 14/756,829

(22) Filed: Oct. 20, 2015

(65) Prior Publication Data

US 2017/0006744 P1 Jan. 5, 2017

(30) Foreign Application Priority Data

Jul. 3, 2015 (QZ) ..... PBR 2015/1557

(51) Int. Cl.
*A01H 5/02* (2006.01)

(52) U.S. Cl.
USPC ..... Plt./137

(58) Field of Classification Search
USPC ..... Plt./101, 130, 137
See application file for complete search history.

*Primary Examiner* — Susan McCormick Ewoldt
*Assistant Examiner* — Karen Redden
(74) *Attorney, Agent, or Firm* — Buchanan Ingersoll & Rooney PC

(57) ABSTRACT

A new and distinct Hybrid Tea rose plant is provided that forms abundantly and substantially continuously attractive very double well-configured luminous light pink blossoms which display a strong fragrance. The growth habit is bushy, and very strong vegetation is formed. The dark green vegetation is dense and bears a semi-glossy aspect on the upper surface that contrasts nicely with the light pink blossom coloration. The disease tolerance is very good particularly with respect to black spot. The plant is well suited for providing attractive ornamentation in parks and gardens.

1 Drawing Sheet

Figures 1, 2, 3, 4, 5, 6, 7, 8, 9, 10, 11, 12, 13, 14:
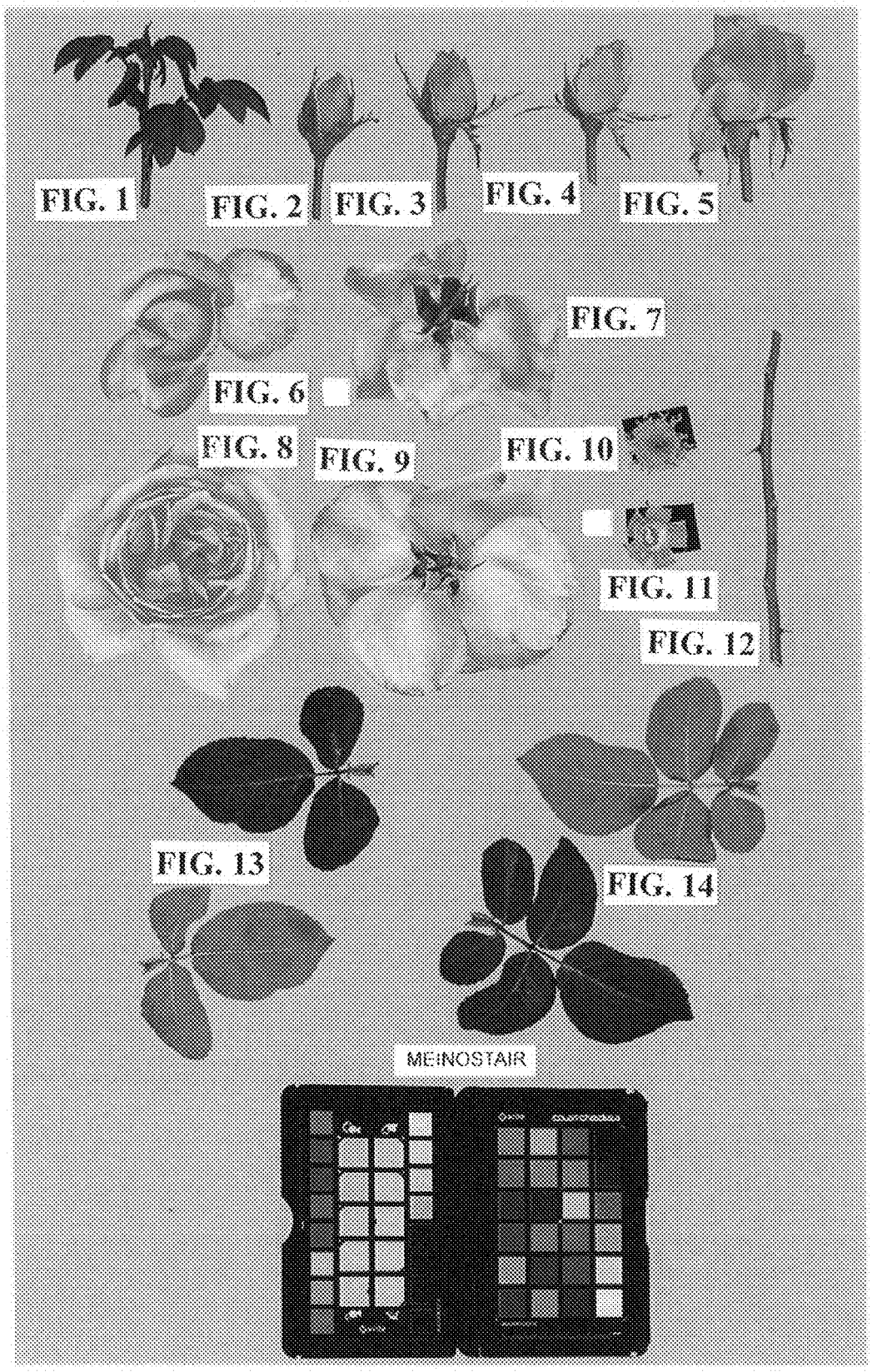

Botanical/commercial classification: *Rosa hybrida*/Hybrid Tea Rose Plant.

Varietal denomination: cv. Meinostair.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meironsse' variety (U.S. Plant Pat. No. 8,496) and 'Ausmas' variety (non-patented in the United States). The male parent (i.e., the pollen parent) was the 'Baipeace' variety (U.S. Plant Pat. No. 14,731).

The parentage of the new variety can be summarized as follows:

('Meironsse'×'Ausmas')×'Baipeace'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a bushy growth habit with very strong vegetation, (b) forms in abundance on a substantially continuous basis attractive very double well-configured luminous light pink blossoms which display a strong fragrance, (c) exhibits dense semi-glossy dark green foliage that contrasts nicely with the light pink blossom coloration, (d) displays very good disease tolerance particularly with respect to black spot, and (e) is well suited for providing attractive ornamentation in parks and gardens.

The blooming tends to commence early in the season during observations to date. The open blossoms commonly display a pleasing substantially uniform well-configured appearance.

The new variety well meets the needs of the horticultural industry and can be grown to advantage in the landscape where attractive ornamentation is to be provided.

The new variety can be readily distinguished from its ancestors. More specifically, the 'Meironsse' variety displays darker colored blossoms that are Indian Orange edged with Capsicum Red. The 'Ausmus' variety forms dissimilar yellow blossoms, the 'Baipeace' variety forms dissimilar golden-yellow blossoms with carmine-pink margins, and the ('Meironsse'×'Ausmas') variety, which is the seed parent, forms dissimilar medium pink blossoms with a smaller diameter than the new variety.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meinostair'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one and one-half year of age and were observed during July while growing outdoors on their own roots at Le Cannet des Maures, Var, France. Standard color information is included at the bottom of the photograph.

FIG. 1—illustrates a specimen of a young shoot;

FIG. 2—illustrates a specimen of a floral bud at the opening of the sepals;

FIG. 3—illustrates a specimen of a floral bud at the further opening of the sepals;

FIG. 4—illustrates a specimen of a floral bud at the opening of the petals;

FIG. 5—illustrates a specimen of a flower in the course of opening.

FIG. 6—illustrates a specimen of a newly open flower—plan view—obverse;

FIG. 7—illustrates a specimen of a newly open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates specimens of leaves with three leaflets—plan view—upper surface (above) and—under surface (below); and FIG. 14—illustrates specimens of leaves with five leaflets—plan view—under surface (above) and—upper surface (below).

DETAILED BOTANICAL DESCRIPTION

The chart used in the identification of the colors is that of The Royal Horticultural Society ("R.H.S.") (R.H.S. Colour Chart, 2001 Edition). The description is based on the observation of one and one-half year old plants during July while growing outdoors as their own roots at Le Cannet des Maures, Var, France.

Class: Hybrid Tea.

Plant:

*Growth habit*.—Bushy.

*Vegetation*.—Very strong.

*Height*.—Commonly near 100 to 120 cm on average.

*Width*.—Commonly near 50 to 70 cm on average.

Branches:

*Color*.—Young stems: near Yellow-Green Group 146B. Adult wood: near Green Group 138B.

*Thorns*.—On young stems-small prickles: commonly absent. On young stems-long prickles: configuration: with an oval and narrow base. Quantity: approximately 4 on average on a stem length of 10 cm. Length: approximately 8 mm on average. Color: near Greyed-Purple Group 187D. On adult stems-small prickles: Configuration: oval and narrow base. Quantity: approximately 4 on average over a stem length of 10 cm. Length: approximately 4 mm on average. Color: near Greyed-Orange Group 174B. On adult stems-long prickles: Configuration: oval and narrow base. Quantity: approximately 4 on average on a stem length of 10 cm. Length: approximately 6 mm on average. Color: near Greyed-Orange Group 178A.

Leaves:

*Stipules*.—Adnate, pectinate, and narrow, approximately 1.2 cm in length on average, approximately 2 mm in width on average, near Green Group 138B on the upper surface, and near Yellow-Green Group 146B on the under surface.

*Petioles*.—Upper surface: near Green Group 138A more or less suffused with Red-Purple Group 59A. Under surface: near Green Group 138B more or less suffused with near Red-Purple Group 59A. Length: approximately 2.7 cm on average for the terminal leaflet. Diameter: commonly near 2 mm on average. Texture: generally smooth and non-glandular on the upper surface, and commonly with a few prickles on the under surface.

*Rachis*.—Upper surface: near Green Group 138A more or less suffused with Red-Purple Group 59A. Under surface: near Green Group 138B more or less suffused with near Red-Purple Group 59A. Length: commonly approximately 3.5 to 4.5 cm on average. Diameter: commonly approximately 1 to 2 mm on average.

*Leaflets*.—Number 3, 5 (most often), and 7. Shape: generally elliptical with an acute tip and a rounded base. Size: the terminal leaflets commonly are approximately 5 cm in length on average and approximately 4 cm in width on average. Edges: slightly denticulate. Serration: small and single (as illustrated). Texture: physically firm and leathery. Color (young foliage): Upper surface: near Green Group 137A amply suffused with near Greyed-Purple Group 187B. Under surface: near Green Group 137D amply suffused with near Greyed-Purple Group 183B. Color (adult foliage): Upper surface: near Green Group 138A more or less suffused with near Red-Purple Group 59A. Under surface: near Green Group 138B more or less suffused with near Red-Purple Group 59A.

Inflorescence:

*Number of flowers*.—Commonly 1 blossom per stem, and commonly 10 to 25 blooms per plant on average.

*Peduncle*.—Commonly smooth, approximately 4.5 cm in length on average, approximately 3 mm in diameter on average, and near Yellow-Green Group 146B more or less suffused with near Greyed-Purple Group 183A.

*Sepals*.—Upper surface: tomentose and near Yellow-Green Group 146B in coloration. Under surface: generally smooth and near Yellow-Green Group 146B in coloration. Shape: longish and broad, and somewhat upright at the base. Size: approximately 3.3 cm in length on average, and approximately 1 cm in width at the widest point on average. Number: commonly 5 on average.

*Buds*.—Shape: substantially conical. Size: small. Length: approximately 2.5 cm on average. Width: approximately 1.8 cm at the widest point on average.

Color as calyx breaks: Near Red Group 44D on the upper surface, and near Orange-Red Group 33A on the under surface.

*Flower*.—Shape: cup-shaped. Diameter: approximately 10 cm on average. Depth: approximately 5 to 6 cm on average. Color (in the course of opening): Upper surface: near Red Group 48D with a spot of near Yellow Group 11B at the base. Under surface: near Red Group 54D with a spot of near Yellow Group 11C at the base. Color (open flower): Upper side: near Red Group 51D with a spot of near Yellow Group 11B at the base. Under side: near Red Group 50D with a spot of near Yellow Group 11C at the base. Fragrance: strong. Petal number: approximately 48 on average under normal growing conditions. Petal shape: with a cuneiform base and rounded tip. Petal texture: leathery and somewhat firm. Petal length: approximately 6 cm on average. Petal width: approximately 5 cm on average. Petal arrangement: imbricated, and without petaloids. Petal drop: good with the petals commonly detaching cleanly before drying. Stamen number: approximately 145 on average. Anthers: regularly arranged around the styles, approximately 2 mm in size on average, and near Greyed-Orange Group 163B in coloration. Filaments: approximately 5 mm in length on average, and near Orange Group 28B in coloration. Pollen: none available for observation. Pistils: approximately 106 on average. Stigmas: approximately 1 mm in size on average, and near Red Group 45D in coloration. Styles: approximately 4 mm in length on average, and near Greyed-Yellow 160D in coloration. Receptacle: smooth, pitcher-shaped in longitudinal section, approximately 9 mm in length and width on average, and near Yellow-Green Group 146B in coloration.

Development:

*Vegetation*.—Very strong.

*Blooming*.—Early season, abundant and substantially continuous.

*Tolerance to diseases*.—Very good particularly with respect to black spot.

The new 'Meinostair' variety has not been observed under all possible environmental conditions to date. Accordingly, it is possible that the phenotypic expression may vary somewhat with changes in light intensity and duration, cultural practices, and other environmental conditions.

I claim:

1. A new and distinct Hybrid Tea rose plant characterized by the following characteristics:

(a) displays a bushy growth habit with very strong vegetation, (b) forms in abundance on a substantially continuous basis attractive very double well-configured luminous light pink blossoms which display a strong fragrance, (c) exhibits dense semi-glossy dark green foliage that contrasts nicely with the light pink blossom coloration, (d) displays very good tolerance to disease particularly with respect to black spot, and (e) is well suited for providing attractive ornamentation in parks and gardens;

substantially as shown and described.

* * * * *

MEINOSTAIR